(12) United States Patent
Kudo et al.

(10) Patent No.: US 7,169,580 B1
(45) Date of Patent: Jan. 30, 2007

(54) PROTEIN HAVING PGE2 SYNTHASE ACTIVITY AND USE THEREOF

(75) Inventors: Ichiro Kudo, 28-15, Minamisenzoku 1-chome, Ota-ku, Tokyo 145-0063 (JP); Makoto Murakami, Tokyo (JP); Sachiko Oh-ishi, Tokyo (JP)

(73) Assignees: Chugai Seiyaku Kabushiki Kaisha, Tokyo (JP); Ichiro Kudo, Tokyo (JP)

( * ) Notice: Subject to any disclaimer, the term of this patent is extended or adjusted under 35 U.S.C. 154(b) by 358 days.

(21) Appl. No.: 10/182,233

(22) PCT Filed: Aug. 25, 2000

(86) PCT No.: PCT/JP00/05758

§ 371 (c)(1),
(2), (4) Date: Dec. 27, 2002

(87) PCT Pub. No.: WO01/57225

PCT Pub. Date: Aug. 9, 2001

(30) Foreign Application Priority Data

Feb. 3, 2000 (JP) .............................. 2000-032704

(51) Int. Cl.
*C12P 31/00* (2006.01)
*C12N 9/02* (2006.01)
*A61K 31/19* (2006.01)

(52) U.S. Cl. .......................... 435/63; 435/189; 514/573
(58) Field of Classification Search .................. 435/63, 435/189, 233

See application file for complete search history.

(56) References Cited

U.S. PATENT DOCUMENTS 6,395,502 B1 * 5/2002 Jakobsson et al. ............ 435/26

FOREIGN PATENT DOCUMENTS

WO    WO 00/28022    5/2000

OTHER PUBLICATIONS

Johnson et al., Mol. Cell Biol. 14(3):1956-1963, 1994.*
Jakobsson et al (Jun. 1999) PNAS, vol. 96, pp. 7220-7225.*
Tanioka et al. (Oct. 20, 2000) J. Biol. Chem., vol. 275, pp. 32775-32782.*
Murakami et al. (Oct. 20, 2000) J. Biol. Chem., vol. 275, pp. 32783-32792.*
Tanioka et al., "Purification and Characterization of Inducible Protaglandin $E_2$ Synthase", *Seikagaku*, vol. 71(8), pp. 2P-443 (1999) (Translation of Japanese Reference).
Kudo et al., "Functional coupling between the enzymes involved in the cyclooxygenase pathway", *Seikagaku*, vol. 71(8), pp. S-213 (1999) (Translation of Japanese Reference).
Urade, et al., "Prostaglandin D, E, and F synthases", *J. Lipid Mediators Cell Signalling*, vol. 12 (2-3), pp. 257-273 (1995).
Watanabe et al., "Two Types of Microsomal Prostaglandin E Synthase: Glutathioe-Dependent and—Independent Prostaglandin E Synthase", *Biochemical and Biophysical Research Communications*, vol. 235(1), pp. 148-152 (1997).
Naraba et al., "Segregated Coupling of Phospholipases $A_2$, Cyclooxygenases and Terminal Prostanoid Synthases in Different Phases of Protanoid Biosynthesis in Rat Peritoneal Macrophages$_1$", *The Journal of Immunology* vol. 160(6), pp. 2974-2982 (1998).
Matsumoto et al., "Concordant Induction of Prostaglandin $E_2$ Synthase with Cyclooxygenase-2 Leads to Preferred Production of Prostaglandin $E_2$ over Thromboxane and Prostaglandin $D_2$ in Lipopolysaccharide-Stimulated Rat Peritoneal Macrophages", *Biochemical and Biophysical Research Communications*, vol. 230(1), pp. 110-114 (1997).
Brock et al., "Arachidonic Acid Is Preferentially Metabolized by Cyclooxygenase-2 to Prostacyclin and Prostaglandin $E_2$ ", *The Journal of Biological Chemistry*, vol. 274(17), pp. 11660-11666 (1999).
Yokota et al., "Stimulation of Prostaglandin $E_2$ Synthesis in Cloned Osteoblastic Cells of Mouse (MC3T3-E1) by Epidmeral Growth Factor", *The Journal of Biological Chemistry*, vol. 261(33), pp. 15410-15415 (1986).
Watanabe et al., "Purification and characterization of membrane-bound prostaglandin E synthase from bovine heart", *Biochimica et Biophysica Acta*, vol. 1439(3), pp. 406-414 (1999).
"Nonsteroidal Anti-Inflammatory Agents" AHFS Drug Information pp. 1571-1584 (1998).
Ogorochi, T et al. "Purification and Properties of Prostaglandin H-E Isomerase from the Cytosol of Human Brain: Identification as Anionic Forms of Glutathione S-Transferase" Journal of Neurochemistry, vol. 48 (3), pp. 900-909 (1987).
Portanova JP, et al. "Selective Neutralization of Prostaglandin $E_2$ Blocks Inflammation, Hyperalgesia, and Interleukin 6 Production In Vivo", J. Exp. Med., vol. 184, pp. 883-891 (1996).
Vane, J.R. and M. Botting "New insights into the mode of action of anti-inflammatory drugs" Inflamm Res., vol. 44 (1), pp. 1-10 (1995).

* cited by examiner

*Primary Examiner*—Elizabeth Slobodyansky
(74) *Attorney, Agent, or Firm*—Fish & Richardson P.C.

(57) ABSTRACT

A single protein which is the substance of the PGE2 synthesis activity in brain soluble fractions of LPS administered rats has been purified and identified. The protein has an activity of synthesizing PGE2 from PGH2, and further, has an activity of synthesizing PGE2 from arachidonic acid in combination with COX.

2 Claims, 12 Drawing Sheets

```
       10        20        30        40        50        60
ATGCAGCCTGCTTCTGCAAAGTGGTACGATCGAAGGGACTATGTCTTCATTGAATTTTGT
 M  Q  P  A  S  A  K  W  Y  D  R  R  D  Y  V  F  I  E  F  C
                         10                                20

70        80        90       100       110       120
GTTGAAGACAGTAAGGATGTTAATGTAAATTTTGAAAAATCCAAACTTACATTCAGTTGT
 V  E  D  S  K  D  V  N  V  N  F  E  K  S  L  T  F  S  C
                         30                                40

130       140       150       160       170       180
CTCGGAGGAAGTGATAATTTTAAGCATTTAAATGAAATTGATCTTTTTCACTGTATTGAT
 L  G  G  S  D  N  F  K  H  L  N  E  I  D  L  F  H  C  I  D
                         50                                60

190       200       210       220       230       240
CCAAATGATTCCAAGCATAAAAGAACGGACAGATCAATTTTATGTTGTTTACGAAAAGGA
 P  N  D  S  K  H  K  R  T  D  R  S  I  L  C  C  L  R  K  G
                         70                                80

250       260       270       280       290       300
GAATCTGGCCAGTCATGGCCAAGGTTAACAAAAGAAAGGGCAAAGCTTAATTGGCTTAGT
 E  S  G  Q  S  W  P  R  L  T  K  E  R  A  K  L  N  W  L  S
                         90                               100

310       320       330       340       350       360
GTCGACTTCAATAATTGGAAAGACTGGGAAGATGATTCAGATGAAGACATGTCTAATTTT
 V  D  F  N  N  W  K  D  W  E  D  D  S  D  E  D  M  S  N  F
                        110                               120

370       380       390       400       410       420
GATCGTTTCTCTGAGATGATGAACAACATGGGTGGTGATGAGGATGTAGATTTACCAGAA
 D  R  F  S  E  M  M  N  N  M  G  G  D  E  D  V  D  L  P  E
                        130                               140

430       440       450       460       470       480
GTAGATGGAGCAGATGATGATTCACAAGACAGTGATGATGAAAAAATGCCAGATCTGGAG
 V  D  G  A  D  D  D  S  Q  D  S  D  D  E  K  M  P  D  L  E
                        150                               160

TAA
 *
```

FIG. 5

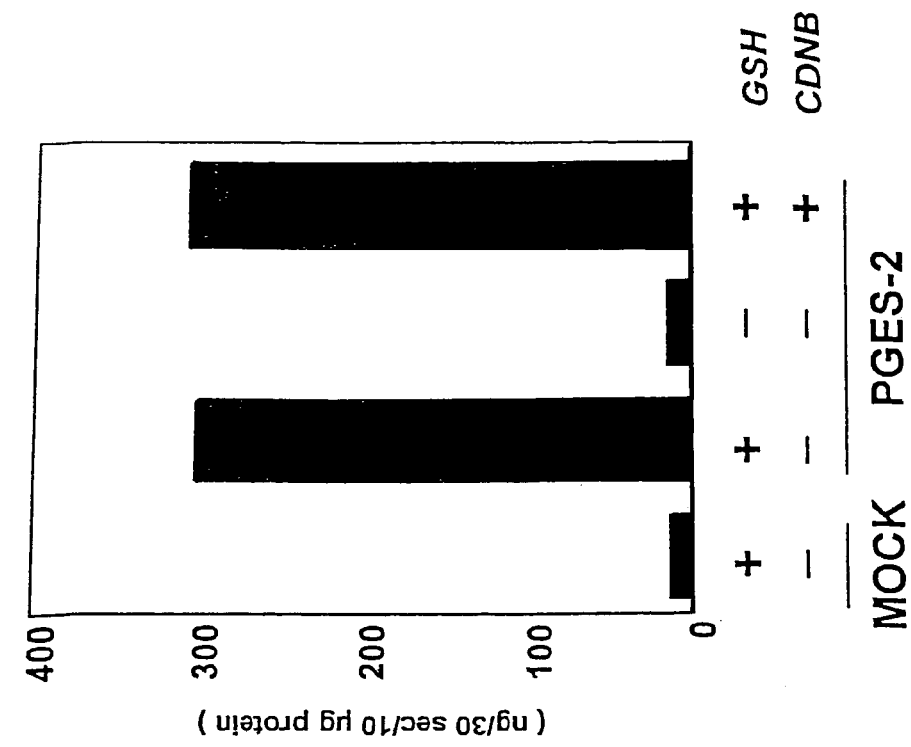
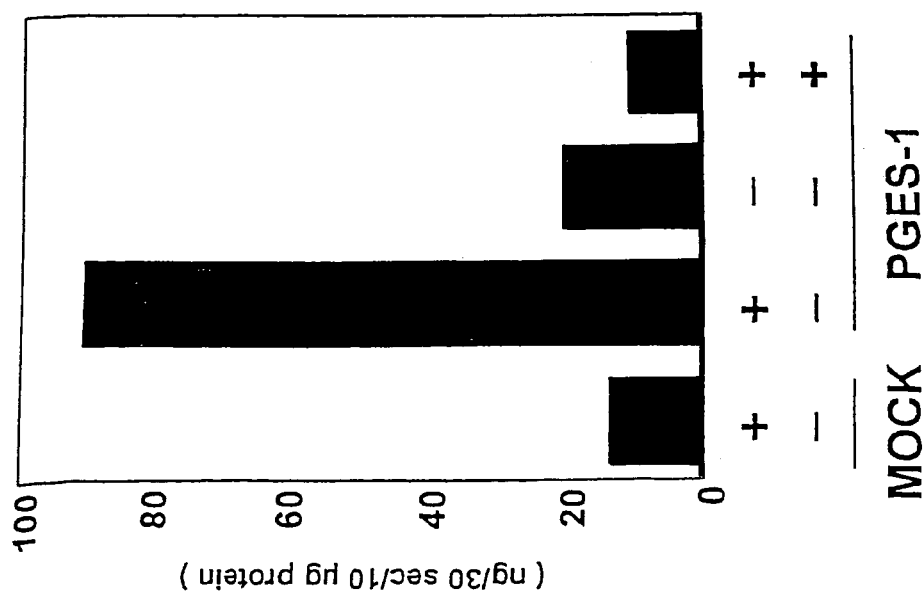
FIG. 6

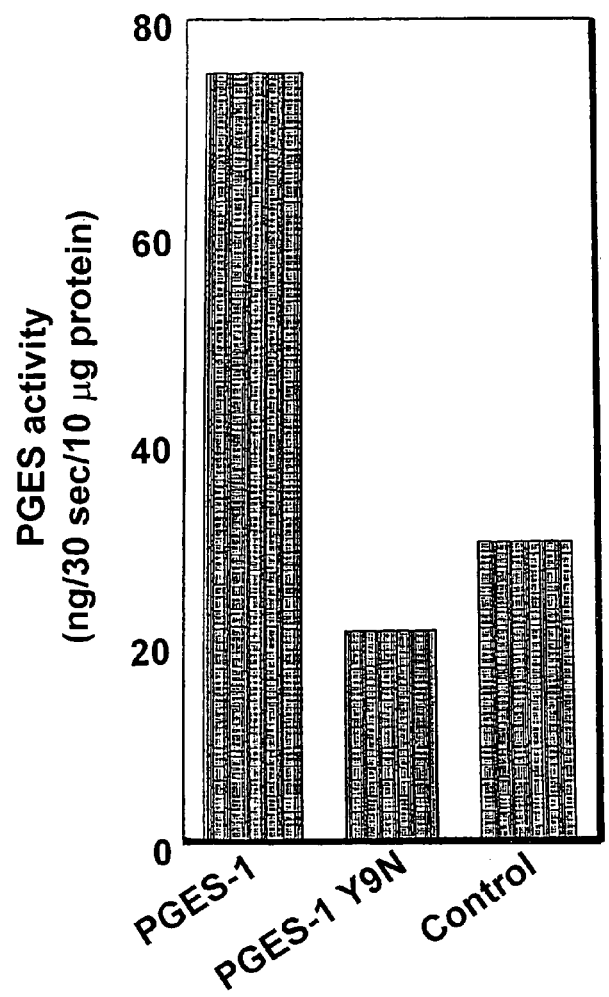
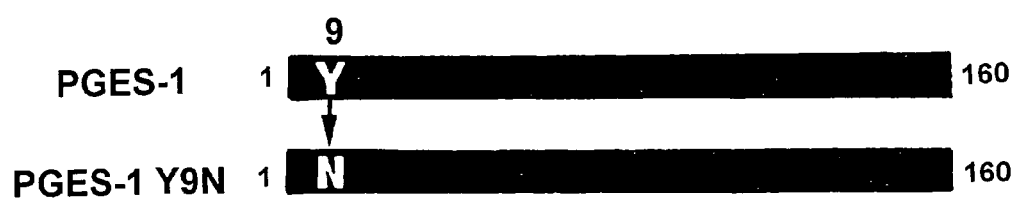
FIG. 7

SEQUENCE LISTING

```
<160> NUMBER OF SEQ ID NOS: 2

<210> SEQ ID NO 1
<211> LENGTH: 160
<212> TYPE: PRT
<213> ORGANISM: Homo sapiens

<400> SEQUENCE: 1

Met Gln Pro Ala Ser Ala Lys Trp Tyr Asp Arg Arg Asp Tyr Val Phe
1               5                   10                  15

Ile Glu Phe Cys Val Glu Asp Ser Lys Asp Val Asn Val Asn Phe Glu
            20                  25                  30

Lys Ser Lys Leu Thr Phe Ser Cys Leu Gly Gly Ser Asp Asn Phe Lys
        35                  40                  45

His Leu Asn Glu Ile Asp Leu Phe His Cys Ile Asp Pro Asn Asp Ser
    50                  55                  60

Lys His Lys Arg Thr Asp Arg Ser Ile Leu Cys Cys Leu Arg Lys Gly
65                  70                  75                  80

Glu Ser Gly Gln Ser Trp Pro Arg Leu Thr Lys Glu Arg Ala Lys Leu
                85                  90                  95

Asn Trp Leu Ser Val Asp Phe Asn Asn Trp Lys Asp Trp Glu Asp Asp
            100                 105                 110

Ser Asp Glu Asp Met Ser Asn Phe Asp Arg Phe Ser Glu Met Met Asn
        115                 120                 125

Asn Met Gly Gly Asp Glu Asp Val Asp Leu Pro Glu Val Asp Gly Ala
    130                 135                 140

Asp Asp Asp Ser Gln Asp Ser Asp Glu Lys Met Pro Asp Leu Glu
145                 150                 155                 160

<210> SEQ ID NO 2
<211> LENGTH: 483
<212> TYPE: DNA
<213> ORGANISM: Homo sapiens
<220> FEATURE:
<221> NAME/KEY: CDS
<222> LOCATION: (1)...(480)

<400> SEQUENCE: 2 atg cag cct gct tct gca aag tgg tac gat cga agg gac tat gtc ttc      48
Met Gln Pro Ala Ser Ala Lys Trp Tyr Asp Arg Arg Asp Tyr Val Phe
1               5                   10                  15 att gaa ttt tgt gtt gaa gac agt aag gat gtt aat gta aat ttt gaa      96
Ile Glu Phe Cys Val Glu Asp Ser Lys Asp Val Asn Val Asn Phe Glu
            20                  25                  30 aaa tcc aaa ctt aca ttc agt tgt ctc gga gga agt gat aat ttt aag     144
Lys Ser Lys Leu Thr Phe Ser Cys Leu Gly Gly Ser Asp Asn Phe Lys
        35                  40                  45
```

```
cat tta aat gaa att gat ctt ttt cac tgt att gat cca aat gat tcc      192
His Leu Asn Glu Ile Asp Leu Phe His Cys Ile Asp Pro Asn Asp Ser
 50                  55                  60 aag cat aaa aga acg gac aga tca att tta tgt tgt tta cga aaa gga      240
Lys His Lys Arg Thr Asp Arg Ser Ile Leu Cys Cys Leu Arg Lys Gly
 65                  70                  75                  80 gaa tct ggc cag tca tgg cca agg tta aca aaa gaa agg gca aag ctt      288
Glu Ser Gly Gln Ser Trp Pro Arg Leu Thr Lys Glu Arg Ala Lys Leu
                 85                  90                  95 aat tgg ctt agt gtc gac ttc aat aat tgg aaa gac tgg gaa gat gat      336
Asn Trp Leu Ser Val Asp Phe Asn Asn Trp Lys Asp Trp Glu Asp Asp
                100                 105                 110 tca gat gaa gac atg tct aat ttt gat cgt ttc tct gag atg atg aac      384
Ser Asp Glu Asp Met Ser Asn Phe Asp Arg Phe Ser Glu Met Met Asn
            115                 120                 125 aac atg ggt ggt gat gag gat gta gat tta cca gaa gta gat gga gca      432
Asn Met Gly Gly Asp Glu Asp Val Asp Leu Pro Glu Val Asp Gly Ala
130                 135                 140 gat gat gat tca caa gac agt gat gat gaa aaa atg cca gat ctg gag      480
Asp Asp Asp Ser Gln Asp Ser Asp Asp Glu Lys Met Pro Asp Leu Glu
145                 150                 155                 160 taa                                                                   483
```

PROTEIN HAVING PGE2 SYNTHASE ACTIVITY AND USE THEREOF

TECHNICAL FIELD

This invention relates to proteins having PGE2 synthase activity and use thereof.

BACKGROUND ART

Nonsteroidal anti-inflammatory drugs (NSAIDs), represented by aspirin and piroxicam, are used widely as antipyretic analgesic antiphlogistic drugs and are considered to manifest anti-inflammatory effects, such as antipyretic, analgesic, and antiphlogistic effects, by suppressing the production of prostaglandins through inhibitory effects on COX (cyclooxygenase). COXs are enzymes that produce PGH2 (prostaglandin H2) from arachidonic acid, and 2 types of enzymes, referred to as constitutive COX-1 and inducible COX-2, are known to exist. Depending on the cell or tissue of production, PGH2 produced by COX is enzymatically converted to PGE2, PGD2, PGF2α, PGI2 (prostacyclin), or TXA2 (thromboxane A2) (Vane J R and Botting R M, Inflammation Research. 44:1, 1995).

In particular, suppression of PGE2 production among the above-mentioned prostanoids is suggested to be important for NSAIDs to show the effect of the drug, due to the fact that PEG2 among these prostanoids is believed to be deeply involved with inflammatory processes, such as pain generation, fever, and edema, and that it exists as the highest concentration at the site of inflammation (Vane J R and Botting R M, Inflammation Research. 44:1, 1995); moreover, the drug efficacies of anti-PGE2 antibody and NSAIDs are reported to be nearly equal in a rat inflammatory model (Portanova J P, Zhang Y, Anderson G D, Hauser S D, Masferrer J L, Seibert K, Gregory S A, Isakson P C, Journal of Experimental Medicine. 184:883–91, 1996).

On the other hand, NSAIDs, apart from PGE2, also suppress the production of PGD2, PGF2α, PGI2, and TXA2 by inhibiting COX, and thus, may exhibit not only anti-inflammatory effects but also effects based on the suppression of the production of these other prostanoids. For example, childbirth is known to be delayed by the inhibition of uterine contraction at the time of delivery due to suppression of PGF2α production, and blood coagulation is known to be delayed by the suppression of TXA2 production (AHFS Drug Information98, p1571 McEnvoy G K Ed., American Society of Health-System Pharmacists, 1998).

Therefore, substances that specifically inhibit the action of PGE2, such as PGE2 synthase (PGES) inhibitors, are expected to serve as excellent anti-inflammatory drugs with lower side effects, by specifically suppressing PGE2 production without suppressing the production of other prostanoids.

To date, although synthases specific for PGD2, PGF2α, PGI2, and TXA2, respectively, have been identified, those for PGE2 synthase have been suggested to exist but have not yet been identified.

Recently, Per-Johan Jakobsson et al. identified a membrane-bound human PGE2 synthase for the first time (Proc. Natl. Acad. Sci. U.S.A., 96:7220–7225, 1999) (herein, the enzyme is referred to as "PGES-2").

On the other hand, the existence of other enzymes with characteristics different from the PGES-2 has been also suggested. Specifically, Ogorochi et al. have estimated that PGES-2 and a protein of pI5.4 with PEGS activity existing in the cytoplasm of human brain are identical, because the proteins are purified together with glutathione S-transferase (GST) (Ogorochi T, Ujihara M., and Narumiya S., J. Neurochem., 48:900–909, 1987).

DISCLOSURE OF THE INVENTION

The object of the present invention is to identify proteins having PGE2 synthase activity, and to provide a use for the proteins. According to one embodiment, the present invention provides methods for producing PGE2 using the protein. In another embodiment, methods for screening PGE2 synthase inhibitors using cells expressing the protein are provided. According to a preferred embodiment, the invention provides methods for screening PGE2 synthase inhibitors using cells co-expressing PGE2 synthase and COX.

The present inventors discovered that the ability to synthesize PGE2 is remarkably induced in the soluble fraction of LPS-administered rat brain Based on this finding, the present inventors vigorously conducted research to identify the substance responsible for the PGE2 synthesis activity in these fractions. And as a result, the inventors succeeded in identifying and purifying a single protein, which is the substance responsible for the activity.

A database search using the amino acid sequence of the obtained protein demonstrated a surprising result, which demonstrated the protein to be identical to a protein reported as human progesterone receptor complex component protein (Johnson J L et al., Mol. Cell. Biol., 14:1956–63, 1994).

Further, a cDNA encoding the obtained protein was inserted into an expression vector to transfect HEK293 cells. A glutathione (GSH)-dependent PGE2 synthesis activity (PGES activity) was observed in the cell lysate of the transfected cells, and the activity was suppressed by 1-chloro-2,4-dinitrobenzene (CDNB), a GST inhibitor. Thus, the cDNA isolated by the present inventors was confirmed to encode the object PGES (the protein was dubbed "PGES-1"). The protein, which had been reported as progesterone receptor complex component protein, was demonstrated to be a protein belonging to PGES.

In addition, the present inventors discovered that screening for PGES inhibitors is enabled by utilizing a system that produces PGE2 from PGH2 using cells made to express PGES-1. However, PGH2, a direct substrate of PGES, is extremely chemically unstable and decomposes non-enzymatically. Thus, construction of a system for screening PGES inhibitors, which is more stable than that wherein PGH2 is added to PGES-expressing cells, is desired in the art. The present inventors presumed that a stable screening system may be constructed by producing human cells that simultaneously express human PGES and human COX, and adding arachidonic acid, a relatively stable substrate of COX, to these cells.

Accordingly, first, the relationship of PGES-1 to COX-1 and COX-2 were examined. The inventors observed that PGE2 production levels increased drastically in the presence of arachidonic acid in cells prepared by transfecting human PGES-1 cDNA to HEK293 cells that express human COX-1 as compared cells without human PGES-1 cDNA transfection. In contrast, human COX-2-expressing HEK293 cells that were made to express PGES-1 did not show an increase in PGE2 production. Cooperative function (coupled function) of COX-1 and PGES-1 was demonstrated. Furthermore, a phenomenon where both enzymes function cooperatively (coupling) was also confirmed in cells expressing both COX-2 and PGES-2. Thus, the present inventors succeeded in establishing a system that produces PGE2 from arachidonic acid by utilizing cells made to express both COX and PGES. This system enables the efficient screening of PGES inhibitors. Compounds isolated by such screening are expected to be applicable as anti-inflammatory drugs and such.

The present invention relates to proteins having PGE2 synthase activity, as well as to methods for producing PGE2 and screening PGE2 synthase inhibitors utilizing the PGE2 synthase activity. Specifically, the present invention provides:

(1) a protein having PGE2 synthase activity, comprising the amino acid sequence of SEQ ID NO: 1;

(2) a protein having PGE2 synthase activity selected from the group of:

(a) a protein comprising the amino acid sequence of SEQ ID NO: 1 in which one or more amino acids are substituted, deleted, added, and/or inserted; and (b) a protein encoded by a DNA that hybridizes under stringent conditions to a DNA consisting of the nucleotide sequence of SEQ ID NO: 1;

(3) the protein of (1) or (2), which is used to synthesize PGE2;

(4) a DNA that encodes the protein of (1) or (2);

(5) a vector containing the DNA of (4);

(6) a transformant carrying the vector of (5);

(7) a method for producing the proteins of (1) or (2), comprising the steps of cultivating the transformant of (6), and collecting the expressed protein from said transformant or from the culture supernatant thereof;

(8) a method for producing PGE2, wherein the protein of (1) or (2) is acted on PGH2;

(9) a method for producing PGE2, wherein COX and PGE2 synthase are acted on arachidonic acid;

(10) the method of (9), wherein COX is COX-1 and PGE2 synthase is the protein of (1) or (2);

(11) the method of (9), wherein COX is COX-2 and PGE2 synthase is PGES-2;

(12) a PGE2 synthesizing agent containing the protein of (1) or (2) as the active ingredient;

(13) a transformant carrying a vector containing a DNA encoding COX and a vector containing a DNA encoding PGE2 synthase;

(14) the transformant of (13), wherein COX is COX-1 and PGE2 synthase is a protein of (1) or (2);

(15) the transformant of (13), wherein COX is COX-2 and PGE2 synthase is PGES-2;

(16) a method of screening for PGE2 synthase inhibitors, comprising the steps of:

(a) contacting the transformant of (6) with a test sample and PGH2;

(b) detecting the level of PGE2 produced by said transformant; and (c) selecting the compound that reduces the level of PGE2 produced as compared with that produced in the absence of the test sample;

(17) a method for screening PGE2 synthase inhibitors, comprising the steps of:

(a) contacting the transformant of any one of (13) to (15) with a test sample and arachidonic acid;

(b) detecting the level of PGE2 produced by said transformant; and (c) selecting the compound that reduces the level of PGE2 produced as compared with that produced in the absence of the test sample;

(18) a PGE2 synthase inhibitor that can be isolated by the screening method of (16) or (17); and

(19) an anti-inflammatory drug containing the PGE2 synthase inhibitor of (18) as the active ingredient.

Herein, the term "PGE2 synthase" refers to enzymes that have the activity to produce PGE2 using PGH2 as substrate. Accordingly, herein, "PGE2 synthase activity" refers to an activity to produce PGE2 using PGH2 as substrate. Moreover, the term "COX" herein refers to enzymes that have the activity to produce PGH2 using arachidonic acid as substrate.

The present invention provides a PGES-1 protein having PGE2 synthase activity. The amino acid sequence of the PGES-1 protein isolated by the present inventors is indicated in SEQ ID NO: 1, and the nucleotide sequence of a cDNA encoding the protein is indicated in SEQ ID NO: 2. The PGES-1 protein was isolated by purifying proteins from soluble fractions of LPS-administered rat brain using the PGE2 synthesizing activity as an index. The primary structure of the PGES-1 protein is identical to the protein reported as human progesterone receptor complex component protein (Johnson J L et al., Mol. Cell Biol., 14:1956–63, 1994); however, the present inventors were the first to find that this protein has PGE2 synthase activity. As described later, the PGES-1 may be utilized to produce PGE2 and to screen PGE2 synthase inhibitors due to the PGE2 synthase activity thereof.

The present invention includes those proteins that are structurally similar to the PGES-1 protein (SEQ ID NO: 1), so long as they retain the PGE2 synthase activity. Such proteins may include, for example, mutants of the PGES-1 protein, allele variants, homologs, and such.

One method well known to those skilled in the art for preparing functionally equivalent proteins is to introduce mutations into proteins. For example, one skilled in the art can prepare mutants that retain PGE2 synthase activity of human PGES-1 proteins by introducing appropriate mutations into the amino acid sequence of the protein (SEQ ID NO: 1), by using site-specific mutagenesis (Hashimoto-Gotoh, T. et al. (1995) Gene 152, 271–275; Zoller, M J, and Smith, M. (1983) Methods Enzymol. 100, 468–500; Kramer, W. et al. (1984) Nucleic Acids Res. 12, 9441–9456; Kramer W, and Fritz H J (1987) Methods Enzymol. 154, 350–367; Kunkel, T A (1985) Proc Natl Acad Sci USA. 82, 488–492; Kunkel (1988) Methods Enzymol. 85, 2763–2766), and such. Mutation of amino acids may occur in nature as well. Thus, a protein comprising the amino acid sequence of human PGES-1 protein (SEQ ID NO:1) in which one or more amino acids are mutated is also included in the present invention, so long as it has PGE2 synthase activity. In such a mutant protein, the number of amino acids mutated is typically 30 residues or less, preferably 10 residues or less, more preferably 5 residues or less (for example 3 residues or less).

It is preferable to mutate an amino acid residue into one that allows the properties of the amino acid side-chain to be conserved. Examples of properties of amino acid side chains include: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chain (R, K, H); and aromatic-containing side-chains (H, F, Y, W) (The letters within parenthesis indicate the one-letter codes of amino acids).

It is well known that a protein having deletion, addition, and/or substitution of one or more amino acid residues in the sequence of the protein can retain the original biological activity (Mark, D. F. et al. Proc. Natl. Acad. Sci. U.S.A.

81:5662–5666 (1984); Zoller, M. J. and Smith, M. Nucleic Acids Res. 10:6487–6500 (1982); Wang, A. et al. Science 224:1431–1433; Dalbadie-McFarland, G. et al. Proc. Natl. Acad. Sci. U.S.A. 79:6409–6413 (1982)).

In the Example of the present invention, it was demonstrated that the substitution of tyrosine, the $9^{th}$ residue from N-terminus of the PGES-1 protein, with an aspartic acid reduces the PGE2 synthase activity. Therefore, this tyrosine residue is suggested to be important for maintaining the PGE2 synthase activity.

An alternative method well known to those skilled in the art for preparing functionally equivalent proteins is, for example, the method utilizing the hybridization technique (Sambrook, J. et al., Molecular Cloning 2nd ed., 9.47–9.58, Cold Spring Harbor Lab. Press, 1989). Generally, one skilled in the art can isolate DNA highly homologous to the whole or part of a DNA sequence encoding human PGES-1 protein (SEQ ID NO: 2), and then isolate a protein functionally equivalent to the human PGES-1 protein from those isolated DNAs. The present invention includes proteins encoded by DNAs that hybridize under stringent conditions to a DNA encoding the human PGES-1 protein, so long as the protein has PGE2 synthase activity. These proteins include, for example, non-human mammalian homologues (e.g. proteins encoded by genes of mice, rats, rabbits, cattle, and such).

Stringent hybridization conditions for isolating a DNA encoding a protein functionally equivalent to human PGES-1 protein may be appropriately selected by a person skilled in the art. For example, prehybridization is performed at 68° C. for 30 min or more using "Rapid-hyb buffer" (Amersham LIFE SCIENCE). A labeled probe is added thereto, and hybridization is conducted by warming at 68° C. for one hour or more. Then, washing in 2×SSC, 0.01% SDS at room temperature for 20 min three times; in 1×SSC, 0.1% SDS at 37° C. for 20 min three times; and then in 1×SSC, 0.1% SDS at 50° C. for 20 min twice. However, several factors, such as temperature and salt concentration, can influence the stringency of hybridization and one skilled in the art can suitably select the factors to accomplish a similar stringency.

In place of hybridization, gene amplification methods using primers synthesized based on the sequence information of the DNA (SEQ ID NO: 2) encoding the human PGES-1 proteins, for example, the polymerase chain reaction (PCR) method, can be utilized for the isolation.

A protein encoded by a DNA isolated through the above hybridization techniques or gene amplification techniques normally has a high homology to the amino acid sequence of the human PGES-1 protein (SEQ ID NO: 1). The proteins of the present invention also include proteins that have a high homology to the amino acid sequence of the human PGES-1 protein, so long as the protein has a PGE2 synthase activity. "Highly homologous" refers to, normally an identity of at least 25% or higher, preferably 40% or higher, more preferably 60% or higher, even more preferably 80% or higher (for example, 90% or higher, 95% or higher) at the amino acid level. The homology of a protein can be determined by following the algorithm in "Wilbur, W. J. and Lipman, D. J. (1983) Proc. Natl. Acad. Sci. USA 80:726–730".

Whether a prepared protein has the PGES synthase activity or not can be detected, for example, by a method described in Example 1.

The proteins of the present invention may have variations in the amino acid sequence, molecular weight, isoelectric point, the presence or absence of sugar chains, form, and so on, depending on the cell or host used to produce it or the purification method utilized Nevertheless, so long as the obtained protein has PGE2 synthase activity, it is within the scope of the present invention. For example, if a protein of the present invention is expressed in a prokaryotic cell, such as E. coli, the protein includes a methionine residue at the N-terminus in addition to the natural amino acid sequence of the protein. Such proteins are also included in the proteins of the present invention.

The proteins of the present invention can be prepared as recombinant proteins or naturally occurring proteins, using methods commonly known in the art. Alternatively, a protein of the present invention can be synthesized artificially. When the protein is a recombinant protein, it may be produced by inserting a DNA (for example, a DNA having the nucleotide sequence of SEQ ID NO: 2) encoding a protein of the present invention into an appropriate expression vector, collecting the transformant obtained by introducing the vector into an appropriate host cell, obtaining an extract, and then purifying and preparing the protein using chromatography, such as ion exchange, reverse phase, or gel filtration; or affinity chromatography using a column immobilized with antibodies against the protein of the invention; or by combining these columns. Alternatively, when a protein of the invention is expressed in host cells (e.g., animal cells or E. coli) as a fusion protein with glutathione S transferase protein, or a recombinant protein with multiple histidine residues, the expressed recombinant protein can be purified using a glutathione column or nickel column After the fusion protein is purified, if necessary, regions of the fusion protein (apart from the desired protein) can be digested and removed with thrombin, factor Xa, etc.

The native protein of the invention can be isolated by methods well known in the art, for example, by purifying an extract of tissues or cells that express a protein of the invention with an affinity column bound using antibodies that bind to a protein of the present invention. The antibodies may be polyclonal or monoclonal antibodies.

The proteins of the invention can be used as PGE2 synthesizing agents. The term "PGE2 synthesizing agents" herein refers to reagents for industrial synthesis of PGE2 or for synthesis of PGE2 for research, and also includes pharmaceutical agents for administration to living bodies.

In addition to being utilized in the above-described in vivo or in vitro production of a protein of the present invention, a DNA encoding a protein of the present invention may also be applied, for example, in the therapy of diseases caused by an aberration in the PGES synthase activity of a protein of the present invention. Any type of DNA, such as cDNA synthesized from mRNA, genomic DNA, or chemical synthetic DNA, can be used, so long as the DNA encodes a protein of the present invention. Further, so long as they can encode a protein of the present invention, DNAs comprising arbitrary sequences based on the degeneracy of the genetic code are also included.

The DNA of the present invention can be prepared using methods known in the art. For example, a cDNA library can be constructed from cells expressing a protein of the present invention and hybridization can be conducted using a part of the DNA sequence of the present invention (for example, SEQ ID NO: 2) as a probe. The cDNA library may be prepared, for example, according to the method described by Sambrook J. et al. (Molecular Cloning, Cold Spring Harbor Laboratory Press (1989)), or instead, commercially available DNA libraries may be used. Alternatively, a DNA of the present invention can be obtained by preparing RNA from cells expressing a protein of the present invention, synthesizing cDNA therefrom using a reverse transcriptase, synthesizing oligo-DNA based on a DNA sequence of the present invention (for example, SEQ ID NO: 2), and amplifying the cDNA encoding a protein of the present invention by PCR using the oligo-DNA as primers.

From the nucleotide sequence of the obtained cDNA, one can determine an open reading frame, and thereby, obtain the amino acid sequence of a protein of the invention. The cDNA obtained may also be used as a probe for screening a genomic DNA library to isolate genomic DNA.

More specifically, mRNA may first be isolated from a cell, tissue, or organ in which a protein of the invention is expressed. Known methods can be used to isolate mRNA; for instance, total RNA may be prepared by the guanidine ultracentrifugation (Chirgwin, J. M. et al., Biochemistry 18:5294–5299 (1979)) or the AGPC method (Chomczynski, P. and Sacchi, N., Anal. Biochem. 162:156–159 (1987)), and mRNA may be purified from total RNA using mRNA Purification Kit (Pharmacia) and such. Alternatively, mRNA may be directly prepared by QuickPrep mRNA Purification Kit (Pharmacia).

The obtained mRNA is used to synthesize cDNA using reverse transcriptase. cDNA may be synthesized using a kit, such as AMV Reverse Transcriptase First-strand cDNA Synthesis Kit (Seikagaku Kogyo). Alternatively, cDNA may be synthesized and amplified following the 5'-RACE method (Frohman, M. A. et al., Proc. Natl. Acad. Sci. U.S.A. 85:8998–9002 (1988); Belyavsky, A. et al., Nucleic Acids Res. 17:2919–2932 (1989)) that uses primers and such described herein; using 5'-Ampli FINDER RACE Kit (Clontech); and by polymerase chain reaction (PCR).

A desired DNA fragment is prepared from the obtained PCR products and linked to a vector DNA. The recombinant vector is used to transform E. coli and such, and the desired recombinant vector is prepared from a selected colony. The nucleotide sequence of the desired DNA can be verified by conventional methods, such as dideoxynucleotide chain termination.

A DNA of the invention may be designed to have a sequence that is expressed more efficiently by taking into account the frequency of codon usage in the host used for expression (Grantham, R. et al., Nucleic Acids Res. 9:r43–74 (1981)). The DNA of the present invention may be altered by a commercially available kit or a conventional method. For instance, the DNA may be altered by digestion with restriction enzymes, insertion of a synthetic oligonucleotide or an appropriate DNA fragment, addition of a linker, or insertion of the initiation codon (ATG) and/or the stop codon (TAA, TGA, or TAG), etc.

The vectors of the present invention are useful in maintaining the DNA of the present invention within the host cell, or expressing a protein of the present invention. When E. coli is used as the host cell, there is no limitation other than that the vector should have an "ori" to amplify and mass-produce the vector in E. coli (e.g., JM109, DH5α, HB101, or XL1Blue), and such; and a marker gene for selecting the transformed E. coli (e.g., a drug-resistance gene selected by a drug (e.g., ampicillin, tetracycline, kanamycin, or chloramphenicol)). For example, M13-series vectors, pUC-series vectors, pBR322, pBluescript, pCR-Script, and such can be used. Besides the vectors, pGEM-T, pDIRECT, pT7, and so on can also be used for subcloning and excision of the cDNA as well. When a vector is used to produce a protein of the present invention, an expression vector is especially useful. When the expression vector is expressed, for example, in E. coli, it should have the above characteristics in order to be amplified in E. coli. Additionally, when E. coli, such as JM109, DH5α, HB101, or XL1-Blue, are used as the host cell, the vector should have a promoter, e.g., the lacZ promoter (Ward et al., (1989) Nature 341:544–546; (1992) FASEB J. 6:2422–2427), the araB promoter (Better et al., (1988) Science 240:1041–1043), or the T7 promoter, that can efficiently promote the expression of the desired gene in E. coli. Other examples of the vectors are pGEX-5x-1 (Pharmacia), "QIAexpress system" (QIAGEN), pEGFP, and pET (for this vector, BL21, a strain expressing T7 RNA polymerase, is preferably used as the host).

Further, the vector may comprise a signal sequence that induces secretion of the polypeptide. For producing the protein in the periplasm of E. coli, the pelB signal sequence (Lei, S. P. et al., J. Bacteriol. 169:4379 (1987)) may be used as the signal sequence for protein secretion. For example, the calcium chloride method or electroporation may be used to introduce the vector into host cells.

Examples of vectors used to produce the proteins of the present invention include, for example, expression vectors other than E. coli, such as expression vectors derived from mammals (e.g., pCDNA3 (Invitrogen), pEGF-BOS (Nucleic Acids Res. (1990) 18(17):5322), pEF, pCDM8), insect cells (e.g., "Bac-to-BAC baculovirus expression system" (GIBCO-BRL), pBacPAK8), plants (e.g. pMH1, pMH2), animal viruses (e.g., pHSV, pMV, pAdexLcw), retroviruses (e.g., pZIPneo), yeasts (e.g., "Pichia Expression Kit" (Invitrogen), pNV11, SP-Q01) and Bacillus subtilis (e.g., pPL608, pKTH50).

In order to express proteins in animal cells, such as CHO, COS, and NIH3T3 cells, the vector should include a promoter necessary for expression in such cells (e.g., the SV40 promoter (Mulligan et al., (1979) Nature 277:108), the MMLV-LTR promoter, the EF1α promoter (Mizushima et al., (1990) Nucleic Acids Res. 18:5322), the CMV promoter, etc.). It is more preferable for the vector to additionally have a marker gene that enables selection of the transformants (for example, a drug resistance gene selected by a drug (e.g., neomycin, G418, etc.)). Examples of vectors with such characteristics include pMAM, pDR2, pBK-RSV, pBK-CMV, pOPRSV, pOP13, and so on.

Furthermore, in order to stably express the gene and to amplify the copy number in cells, the method using CHO cells deficient in nucleic acid synthetic pathways as the host, incorporating into the CHO cells a vector (such as pCHOI) having a DHFR gene that compensates for the deficiency, and amplifying the vector with methotrexate (MTX) can be used. Furthermore, for transiently expressing a gene, the method that transforms COS cells that have the gene for SV40 T antigen on the chromosome with a vector (such as pcD) having the SV40 replication origin can be mentioned. The replication origin may be that of a polyomavirus, adenovirus, bovine papilloma virus (BPV), and the like. Further, to amplify the gene copy number in the host cells, selection markers, such as aminoglycoside transferase (APH) gene, thymidine kinase (TK) gene, E. coli xanthine-guanine phosphoribosyl transferase (Ecogpt) gene, and dihydrofolate reductase (dhfr) gene may be comprised in the expression vector.

A DNA of the present invention can be expressed in animals by, for example, inserting a DNA of the invention into an appropriate vector and introducing the vector into a living body by the retrovirus method, the liposome method, the cationic liposome method, the adenovirus method, and so on. Thus, it is possible to perform gene therapy of diseases caused by a mutation in a gene of the present invention. The vectors used in these methods include, but are not limited to, adenovirus vectors (e.g. pAdexlcw), retrovirus vectors (e.g. pZIPneo), and so on. General techniques for gene manipulation, such as insertion of the DNA of the invention into a vector, can be performed according to conventional methods (Molecular Cloning, 5.61–5.63). Administration to the living body may be performed according to ex vivo methods or in vivo methods.

The host cell into which the vector of the invention is introduced is not particularly limited. For example, *E. coli*, various animal cells, and such, can be used. The host cell of the present invention can be used, for example, as a production system to produce and express a protein of the present invention. Protein production systems include in vitro and in vivo systems. Such production systems using eukaryotic cells or prokaryotic cells can be given as in vitro production systems.

As eukaryotic host cells, for example, animal cells, plant cells, and fungi cells can be used. Mammalian cells, for example, CHO (J. Exp. Med. (1995) 108:945), COS, 3T3, myeloma, BHK (baby hamster kidney), HeLa, Vero, amphibian cells (e.g. platanna oocytes (Valle et al., (1981) Nature 291:358–340), and insect cells (e.g. Sf9, Sf21, Tn5) are known as animal cells. Among CHO cells, those deficient in the DHFR gene, dhfr-CHO (Proc. Natl. Acad. Sci. USA (1980) 77:4216–4220) and CHO K-1 (Proc. Natl. Acad. Sci. USA (1968) 60:1275), are particularly preferable. Among animal cells, CHO cells are particularly preferable for mass expression. A vector can be introduced into a host cell by, for example, the calcium phosphate method, the DEAE-dextran method, methods using cationic liposome DOTAP (Boehringer-Mannheim), electroporation, lipofection, etc.

As plant cells, for example, plant cells originating from *Nicotiana tabacum* are known as protein producing systems and may be used as callus cultures. As fungal cells, yeast cells such as *Saccharomyces*, including *Saccharomyces cerevisiae*, or filamentous fungi such as *Aspergillus*, including *Aspergillus niger*, are known.

Useful prokaryotic cells include bacterial cells. Bacterial cells, such as *E. Coli*, for example, JM109, DH5α, HB101, and such, as well as *Bacillus subtilis* are known.

These cells are transformed by a desired DNA, and the resulting transformants are cultured in vitro to obtain the protein. Transformants can be cultured using known methods. For example, culture medium, such as DMEM, MEM, RPMI1640, or IDMM, may be used with or without serum supplements, such as fetal calf serum (FCS), as culture medium for animal cells. The pH of the culture medium is preferably between about 6 and 8. Such cells are typically cultured at about 30 to 40° C. for about 15 to 200 hr, and the culture medium may be replaced, aerated, or stirred if necessary.

Animal and plant hosts may be used for in vivo production. For example, a desired DNA can be introduced into an animal or plant host. Encoded proteins are produced in vivo, and then recovered. These animal and plant hosts are included in the "host" of the present invention.

Animals to be used for the production system described above include mammals and insects. Mammals, such as goats, pigs, sheep, mice, and cattle, may be used (Vicki Glaser, SPECTRUM Biotechnology Applications (1993)). Alternatively, the mammals may be transgenic animals.

For instance, a desired DNA may be prepared as a fusion gene with a gene such as goat β casein gene that encodes a protein specifically produced into milk. DNA fragments comprising the fusion gene are injected into goat embryos, which are then introduced back to female goats. Desired proteins are then recovered from milk produced by the transgenic goats (i.e., those born from the goats that had received the modified embryos) or by their offspring. To increase the amount of milk containing the proteins produced by transgenic goats, appropriate hormones may be administered to the transgenic goats (Ebert, K. M. et al., (1994) Bio/Technology 12:699–702).

Alternatively, insects, such as silkworm, may be used. Baculoviruses into which a DNA encoding a desired protein has been inserted can be used to infect silkworms, and the desired protein can be recovered from the body fluid (Susumu, M. et al., (1985) Nature 315:592–594).

As plants, for example, tobacco can be used. When using tobacco, a DNA encoding a desired protein may be inserted into a plant expression vector, such as pMON 530, which is introduced into bacteria, such as *Agrobacterium tumefaciens*. Then, the bacteria can be used to infect tobacco, such as *Nicotiana tabacum*, and the desired polypeptide can be recovered from the leaves (Julian, K. -C. Ma et al., (1994) Eur. J. Immunol. 24:131–138).

A protein of the present invention obtained as above may be isolated from inside or outside of host (medium, etc.), and purified as a substantially pure homogeneous protein. The method for protein isolation and purification is not limited to any specific method; in fact, any standard method may be used. For instance, column chromatography, filters, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

For chromatography, for example, affinity chromatography, ion-exchange chromatography, hydrophobic chromatography, gel filtration chromatography, reverse phase chromatography, adsorption chromatography, and such may be used (Strategies for Protein Purification and Characterization: A Laboratory Course Manual. Ed. Daniel R. Marshak et al., Cold Spring Harbor Laboratory Press (1996)). These chromatographies may be performed by liquid chromatographies such as HPLC and FPLC. Thus, the present invention encompasses highly purified proteins produced by the above methods.

A protein may be optionally modified or partially deleted by treating it with an appropriate protein-modifying enzyme before or after purification. For example, trypsin, chymotrypsin, lysylendopeptidase, protein kinase, glucosidase, and such are used as protein-modifying enzymes.

Further, the present invention provides methods for producing PGE2 utilizing a protein of this invention having the PGE2 synthase activity. According to an embodiment, the method is characterized by the treatment of PGH2 with a protein having the PGE2 synthase activity of the invention.

A protein having the PGE2 synthase activity used to produce PGE2 may be a naturally derived protein, a recombinant protein, or an artificially synthesized protein. Moreover, it may be a purified protein or a protein in an intracellularly expressed form. Furthermore, the protein may be immobilized in a reaction system. Since a PGE2 synthase of this invention demonstrates a glutathione (GSH) dependent activity, addition of glutathione to the reaction system is preferred. The PGH2 used for this reaction may be, for example, a commercial product (manufactured by Cayman).

Further, a preferred embodiment of the method for producing PGE2 utilizing the protein of this invention having a PGE2 synthase activity is a method characterized by reacting COX and PGE2 synthase with arachidonic acid. The method takes into consideration the fact that PGH2, which is the direct substrate of PGE2 synthase, is chemically extremely unstable and decomposes non-enzymatically, and thus, produces PGE2 from arachidonic acid, which is a relatively stable precursor of PGH2. Specifically, production of PGE2 from arachidonic acid is achieved by a cooperative action using COX, that produces PGH2 from arachidonic acid, and PGE2 synthase, that produces PGE2 from PGH2.

A PGE2 synthase of this invention and COX used to produce PGE2 may be naturally derived proteins, recombinant proteins, or artificially synthesized proteins. Furthermore, they may be purified proteins or proteins in intracellularly expressed form. Furthermore, the proteins may be immobilized in a reaction system. Since a PGE2 synthase of this invention demonstrates a glutathione (GSH) dependent activity, addition of glutathione to the reaction system is preferred.

PGE2 was demonstrated in the Example to be produced from arachidonic acid by the cooperation of PGES-1 with COX-1, or PGES-2 with COX-2. Therefore, preferred enzymes for use in PGE2 production include the combination of PGES-1 and COX-1, and the combination of PGES-2 and COX-2.

The produced PGE2 may be purified by normal means of purification, for example, distillation under normal pressure or reduced pressure; high-speed liquid chromatography using silica gel or magnesium silicate; thin layer chromatography; column chromatography, washing; recrystallization; and such.

Furthermore, the present invention provides methods of screening for PGE2 synthase inhibitors. According to an embodiment, the screening method of this invention comprises the steps of: (a) contacting a transformant which carries a vector containing a PGES-encoding DNA with a test sample and PGH2; (b) detecting the production level of PGE2 of the cell; and (c) selecting the compound that reduces the production level of PGE2 with that observed in the absence of the contact with the test sample.

The transformant used for the screening can be prepared, for example, by inserting a DNA encoding a PGE2 synthase into a vector, such as pcDNA3.1, and then by introducing this into cells, such as HEK293 cells.

Test samples to be contacted with the transformant include, for example, cell extracts, cell culture supernatants, microorganism fermentation products, marine organism extracts, plant extracts, purified or crude proteins, peptides, non-peptide compounds, synthetic low-molecular-weight compounds, and natural compounds; but are not limited to these examples. The test sample may include antibodies binding to a PGE2 synthase, or antisense oligonucleotides suppressing the expression of the enzyme.

According to a preferred embodiment of the screening method of this invention, the method comprises the steps of: (a) contacting the transformant which carries a vector containing a COX-encoding DNA and a vector containing a PGES-encoding DNA, with a test sample and arachidonic acid; (b) detecting the production level of PGE2 of the transformant; and (c) selecting the compound that reduces the production level of PGE2 compared with that observed in the absence of the contact with the test sample.

The transformant used for the screening can be prepared, for example, by inserting a DNA encoding a PGE2 synthase and a DNA encoding COX, respectively, into vectors, such as pcDNA3.1, and then by co-transfecting them into cells, such as HEK293 cells. The genes to be cotransfected preferably are exemplified by the combination of PGES-1 and COX-1, and the combination of PGES-2 and COX-2. Arachidonic acid to be contacted with the transformant may be, for example, a commercial product (manufactured by Sigma).

Similar to the screening method mentioned above, the test samples include, for example, cell extracts, cell culture supernatants, microorganism fermentation products, marine organism extracts, plant extracts, purified or crude proteins, peptides, non-peptide compounds, synthetic low-molecular-weight compounds, and natural compounds; but are not limited to these examples. Further, the test sample may be antibodies binding to a PGE2 synthase, or antisense oligonucleotides suppressing the expression of the enzyme The PGE2 production level during the screening of the present invention can be measured, for example, by Enzyme Immunoassay (a kit by Cayman). As a result, if the PGE2 production level is reduced by the contact of a test sample with the transformant, compared with that observed in the absence of the contact, the test sample is suggested to be a compound that inhibits the PGE2 synthase activity.

A PGE2 synthase inhibitor, which may be isolated by a screening method of this invention, may be utilized as an anti-inflammatory drug. NSAIDs (nonsteroidal anti-inflammatory drugs), represented by aspirin and piroxicam, which have been used widely as antipyretic analgesic antiphlogistic drugs, suppress the production of PGD2, PGF2a, PGI2, and TXA2, in addition to PGE2 by inhibiting COX. Therefore, NSAIDs not only possess anti-inflammatory effects but also are likely to express effects based on the suppression of the production of these prostanoids (other than the PGE2). On the other hand, since the compounds that can be isolated by the screening of this invention are expected to specifically inhibit a PGE2 synthase, development of medicaments with fewer side effects is enabled.

Furthermore, cells that co-express COX and PGE2 synthase have significantly faster proliferation rates as compared to the control cells, taking on a form similar to a transformant lacking contact inhibition ability, and thus, can be considered as a model system for human clinical cancer suggested to be related to COX2. Therefore, compounds that can be isolated by the screening of this invention may be utilized as anti-cancer drugs.

A compound isolated by the screening of this invention can be as a pharmaceutical agent for humans and other mammals, such as mice, rats, guinea-pigs, rabbits, chicken, cats, dogs, sheep, pigs, cattle, monkeys, baboons, and chimpanzees. Specifically, the isolated compound can either itself be directly administered to subjects or it can be formulated into a pharmaceutical composition using known pharmaceutical preparation methods for administration. For example, according to the need, the drugs can be taken orally, as sugar coated tablets, capsules, elixirs, and microcapsules; or non-orally, in the form of injections of sterile solutions or suspensions with water or any other pharmaceutically acceptable liquid. For example, the compounds can be formulated by mixing appropriately with pharmacologically acceptable carriers or medium, such as, sterilized water, physiological saline, plant-oil, emulsifiers, suspending agents, surfactants, stabilizers, flavoring agents, excipients, vehicles, preservatives, and binders, in a unit dose form required for generally accepted drug implementation. The amount of active ingredient in these preparations makes a suitable dosage within the indicated range acquirable.

Examples of additives that can be mixed for tablets and capsules are; binders such as gelatin, corn starch, tragacanth gum, and arabic gum; excipients such as crystalline cellulose; swelling agents such as corn starch, gelatin, and alginic acid; lubricants such as magnesium stearate; sweeteners such as sucrose, lactose, or saccharin; flavoring agents such as peppermint, Gaultheria adenothrix oil, and cherry. When the unit dosage form is a capsule, a liquid carrier, such as oil, can also be included in the above ingredients. Sterile composites for injections can be formulated following normal drug implementations using vehicles such as distilled water used for injections.

Physiological saline, glucose, and other isotonic liquids including adjuvants, such as D-sorbitol, D-mannnose, D-mannitol, and sodium chloride, can be used as aqueous solutions for injections. These can be used in conjunction with suitable solubilizers, such as alcohol, specifically ethanol, polyalcohols such as propylene glycol and polyethylene glycol, non-ionic surfactants, such as Polysorbate 80 (TM) and HCO-50.

Sesame oil or Soy-bean oil can be used as a oleaginous liquid and may be used in conjunction with benzyl benzoate or benzyl alcohol as a solubilizer or may be formulated with a buffer such as phosphate buffer and sodium acetate buffer, a pain-killer such as procaine hydrochloride, a stabilizer such as benzyl alcohol, phenol, or an anti-oxidant. The prepared injection is generally filled into a suitable ampule.

Methods well known to one skilled in the art may be used to administer a pharmaceutical compound to patients, for example as intraarterial, intravenous, subcutaneous injections and also as intranasal, transbronchial, intramuscular, percutaneous, or oral administrations. The dosage varies according to the body-weight and age of a patient, and the administration method; however, one skilled in the art can suitably select the dosage. If said compound can be encoded by a DNA, the DNA can be inserted into a vector for gene therapy to perform the therapy. The dosage and method of administration vary according to the body-weight, age, and symptoms of a patient, but one skilled in the art can select them suitably.

Although varying according to the symptoms, the dose of a PGE2 synthase inhibitor that can be isolated by the screening methods of this invention is generally in the range of about 0.1 mg to 1 g, preferably about 1.0 to 100 mg, and more preferably about 1.0 to 20 mg per day for adults (body weight: 60 kg) in the case of an oral administration. Although varying according to the subject, target organ, symptoms, and method of administration, a single dose of a compound for parenteral administration is advantageous, for example, when administered intravenously to normal adults (60 kg body weight) in the form of injection, in the range of about 0.01 to 300 mg, preferably about 0.1 to 100 mg, and more preferably about 0.1 to 10 mg per day. Doses converted to 60 kg body weight or per body surface area can be administered to other animals.

BRIEF DESCRIPTION OF THE DRAWINGS

FIG. 5 depicts the nucleotide sequence of p23 (PGES-1) cDNA (SEQ ID NO:2) and the amino acid sequence (SEQ ID NO:1) thereof.

FIG. 6 depicts graphs demonstrating the in vitro enzyme profile of the recombinant PGES-1 and PGES-2 proteins expressed in HEK293 cells. PGES-1 (left panel) was demonstrated to be GSH dependent and CDNB sensitive; whereas PGES-2 (right panel) was demonstrated to be GSH dependent and CDNB insensitive.

FIG. 7 depicts a graph demonstrating the PGES activity of a mutant protein (PGES-1 Y9N), wherein the ninth tyrosine from the N-terminus ($Tyr^9$) is mutated to asparagine. $Tyr^9$ was demonstrated to be essential for the PGES-1 activity.

BEST MODE FOR CARRYING OUT THE INVENTION

The present invention will be described in more detail below by way of Examples, but should not construed as being limited to these Examples.

EXAMPLE 1

Identification of the PGES-1 Protein

PGES activity was measured as follows: Cells suspended in 20 mmol/L Tris-hydrochloride buffer (pH 7.4) were homogenized using ultrasonic homogenizer (Branson Sonifier Model 200) and centrifuged at 800×g for 5 minutes at 4° C., and the supernatant was used as the cell lysate in the following. 0.5 µg of PGH2 was added to the lysate, which was suspended with 0.1 mol/L Tris-hydrochloride buffer (pH 8.0) containing 1 mmol/L GSH, with a protein content of 10 µg, was incubated for 30 seconds at 24° C., and then 8 mmol/L $FeCl_2$ was added to terminate the reaction. The amount of produced PGE2 was measured by Enzyme Immunoassay Kit (Cayman), and PGES activity was expressed as the amount of PGE2 produced per 30 seconds, per 10 µg of protein (ng/30 sec/10 µg protein).

Figure 1:
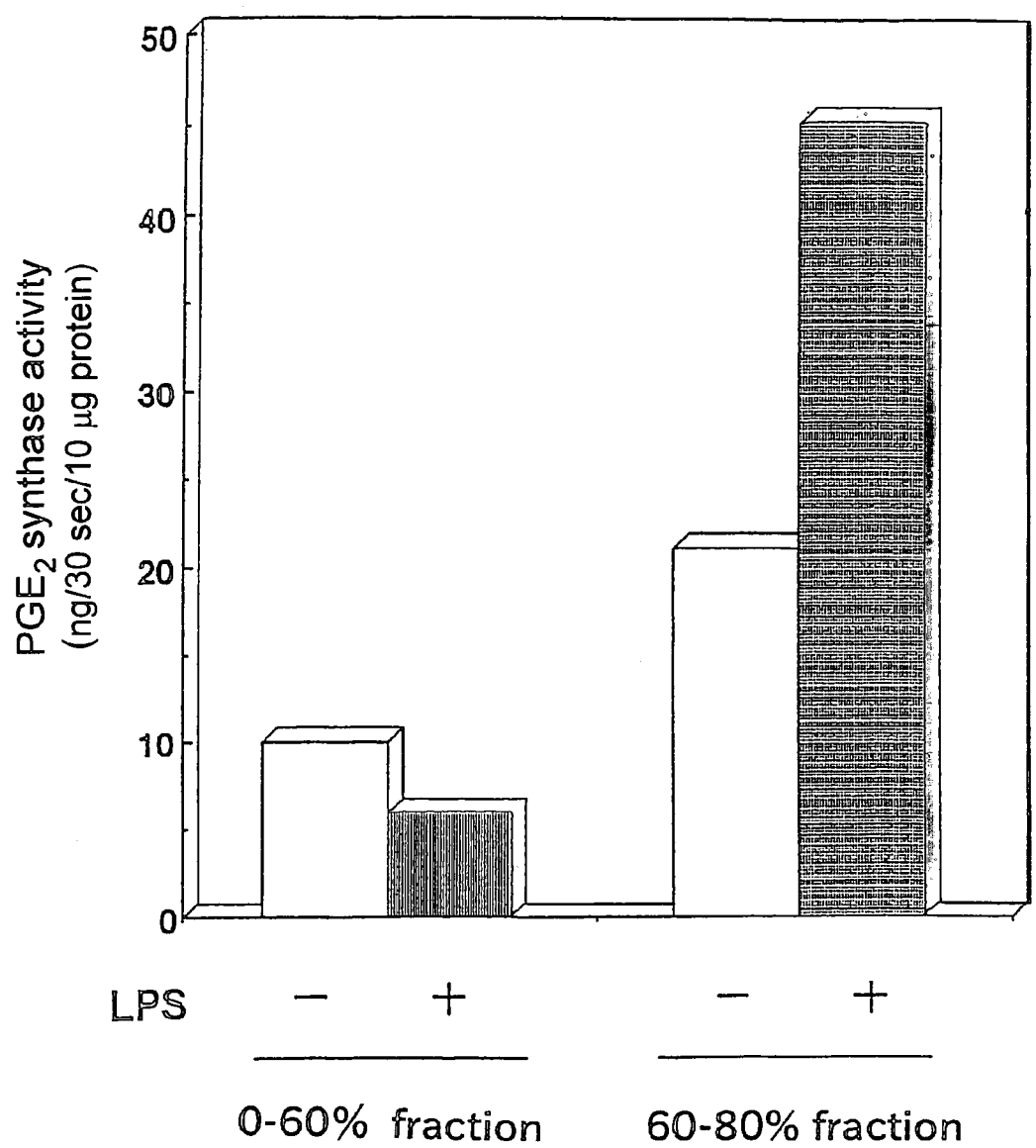
FIG. 1 depicts a graph demonstrating the PGES activity in ammonium sulfate precipitated fraction of the rat brain soluble fraction.
Figure 2:
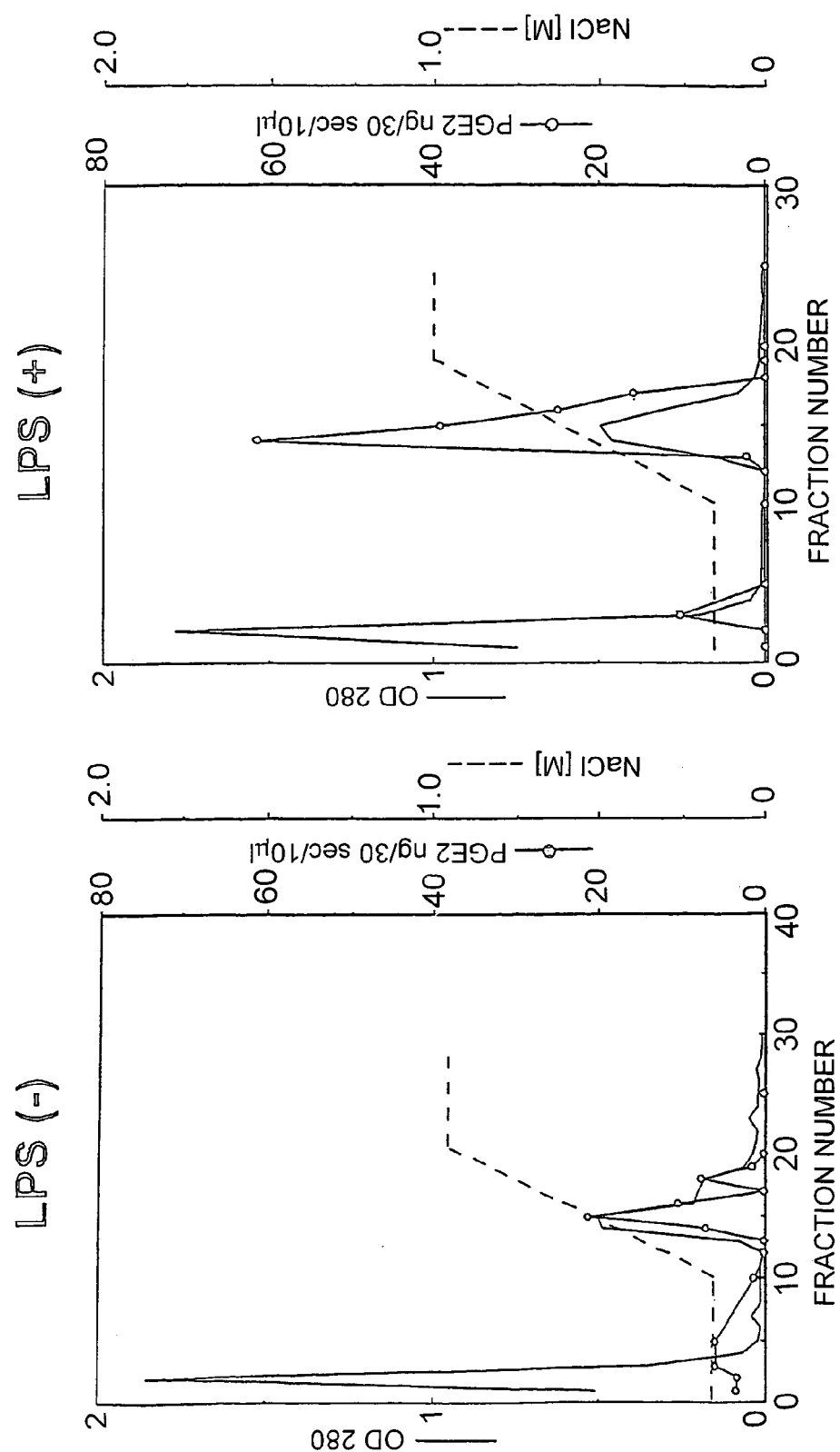
FIG. 2 depicts graphs demonstrating the elution profiles of the PGES activity by DEAE-Sephacel ion exchange column chromatography.

150 µg/kg body LPS (*Salmonella minnesota*: Re595) was administered intravenously from rat tail. Rat brain was removed 2 days after the injection and was homogenized using Potter's homogenizer at 4° C. The homogenate was centrifuged at 10,000×g at 4° C. for 20 minutes, and the supernatant was collected. The supernatant was centrifuged again at 100,000×g at 4° C. for 60 minutes to recover the supernatant. 60 to 80% saturated ammonium sulfate precipitation fractions having PGES activity (FIG. 1) were collected from the supernatant, and fractions having the PGES activity eluted at an NaCl concentration of around 0.5 mol/L to around 0.8 mol/L by DEAE-Sephacel ion exchange column chromatography were collected (FIG. 2).

Furthermore, these fractions were subjected to Superdex 200 column gel filtration FPLC (elution buffer: 20 mmol/L Tris-hydrochloride buffer (pH 7.4), 150 mmol/L NaCl), to yield 3 peaks demonstrating PGES activity: A (molecular weight of approximately 300 kDa); B (molecular weight of approximately 100 kDa); and C (molecular weight of approximately 50 kDa). No significant differences in the peaks A and B were observed in the PGES activity between LPS-administered rats and normal rats; whereas, about 6 times higher PGES activity of peak C was observed in LPS-administered rats compared to normal rats (FIG. 3, top panel).

Figure 3:
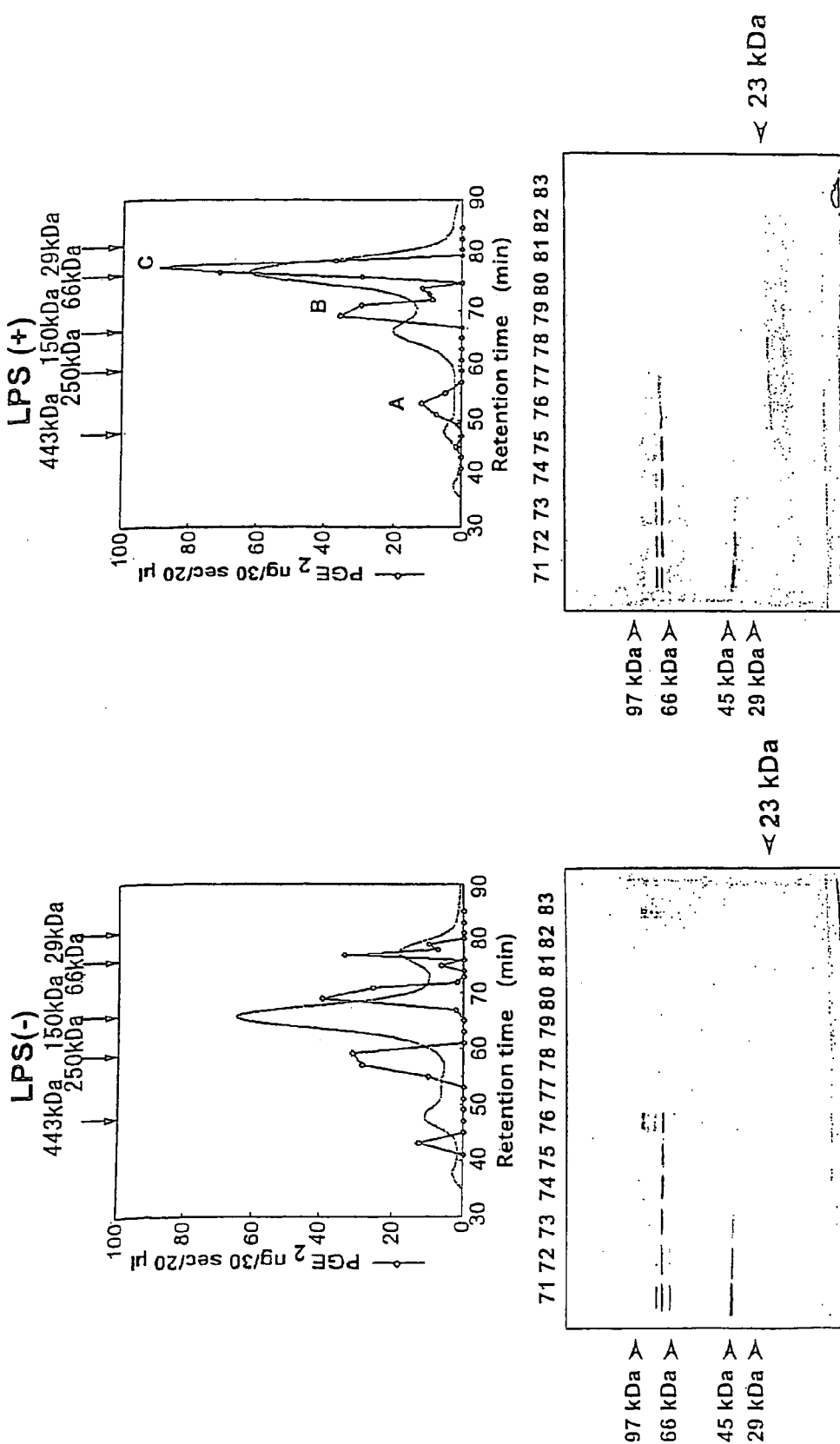
FIG. 3 depicts graphs demonstrating the elution profiles of the PGES activity by Superdex 200 gel filtration column chromatography (top), and photographs demonstrating the results of SDS-PAGE analyses (bottom).
Figure 4:
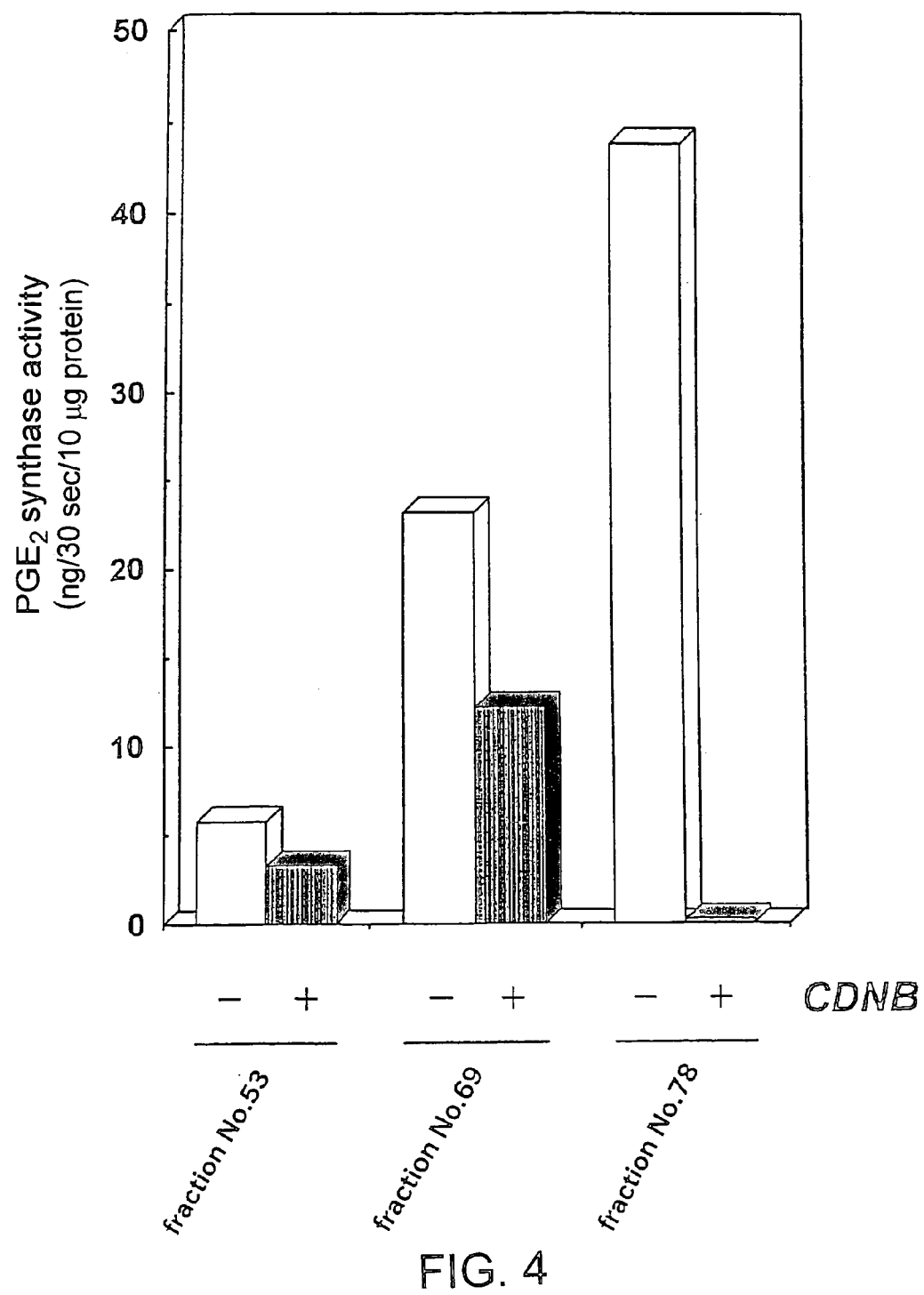
FIG. 4 depicts a graph demonstrating the effect of CDNB on the PGES activity in each fraction obtained by Superdex 200 gel filtration column chromatography.

A protein of a molecular weight of about 27 kDa, corresponding with the PGES activity (PGES-1), was obtained by SDS electrophoretic analysis of peak C (FIG. 3, bottom). The production of this protein was predicted to elevate in response to inflammatory stimulus due to the fact that large amount of the protein was detected in LPS-administered rats than in normal rats. Furthermore, in contrast to peak A and B, peak C was strongly inhibited by CDNB (FIG. 4). Therefore, the protein was suggested to be a GST-like isozyme.

Figure 8:
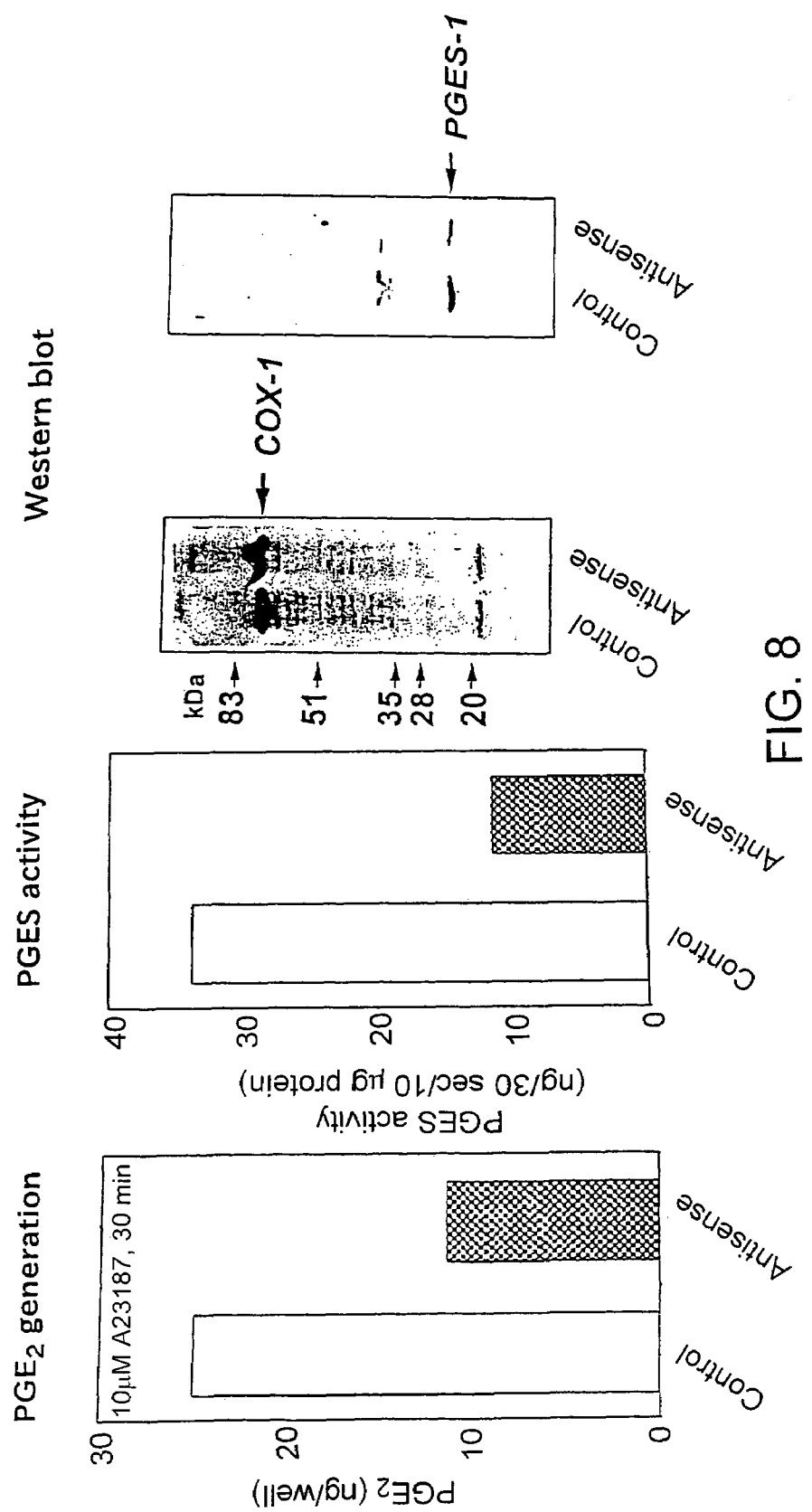
FIG. 8 depicts graphs (left and middle panels) and photographs (right two panels) demonstrating the effect on $PGE_2$ production of the introduced PGES-1 antisense expression vector into 3Y1 cells.

Peptide mapping of PGES-1 protein was carried out using V8 protease, and 3 fragments among the peptide fragments were analyzed by N-terminal amino acid sequence analyzer to determine the partial amino acid sequence thereof. According to GenBank database search with one of these amino acid sequences, the sequence completely matched to a portion of a known sequence reported as the human progesterone receptor complex component protein p23 (Johnson, J L et al., Mol. Cell. Biol., 14:1956–63, 1994). Therefore, referring to the reported cDNA sequence, the cDNA of full-length human progesterone receptor complex component protein p23 was isolated by RT-PCR method using HeLa cell mRNA as the material (FIG. 5) PGES activity dependent to GSH was observed in the cell lysate by inserting the cDNA into expression vector pcDNA3.1, and transfecting HEK293 cells using lipofectamine, which activity was suppressed in the coexistence of CDNB (FIG. 6, left panel). Thus, the cDNA was confirmed to encode the desired PGES. In addition, the mutant protein, wherein the 9th tyrosine residue from the N-terminus was substituted by point mutation to asparagine, did not demonstrate the PGES activity, which elucidated the tyrosine residue to be essential for the expression of the activity (FIG. 7). On the other hand, when pcDNA3.1-hygro, which has the entire PGES-1-encoding region cloned in reverse, was transfected to human fibroblast 3Y1, PGES-1 synthesis was inhibited and PGE2 production and PGES activity was decreased demonstrating the inhibition of PGE2 production by antisense RNA (FIG. 8).

Although a GSH-dependent PGES activity was confirmed in HEK293 cells transfected with PGE2 synthase (PGES-2), an enzyme reported by Per-Johan Jakobsson et al., the activity was not suppressed by the coexistence of CDNB (FIG. 6, right panel) which demonstrates the difference between PGES-1 and PGES-2.

The PGES-1 protein is an enzyme that converts PGH2 produced by COX, particularly by COX-1, into PGE2, and is thought to have an important role in inflammatory reactions where PGE2 plays a major role.

EXAMPLE 2

Preparation of Cells Coexpressing COX and PGES

Human kidney-derived HEK293 cells (human, embryo, kidney, transformed with adenovirus 5 DNA) were purchased from ATCC (ATCC Number: CRL-1573).

Expression vectors wherein human COX-1 and COX-2 cDNAs were inserted into pcDNA3.1, respectively, were transfected into HEK293 cells using lipofectamine to produce HEK293 cells that express either COX-1 or COX-2. HEK293 cells expressing PGES-1 or PGES-2 alone, or coexpressing COX-1 and PGES-1, COX-1 and PGES-2, COX-2 and PGES-1, or COX-2 and PGES-2 were constructed by similarly transfecting expression vectors wherein either human PGES-1 cDNA or human PGES-2 cDNA was inserted into pcDNA3.1 into constructed COX-1 or COX-2 expressing cells and into HEK293 cells of the parent strain, and these cells were used in the following experiment. Evaluation of cell proliferation was performed by seeding the cell on RPMI1640 media in a 6-well plate (Iwaki) at $1.5 \times 10^5/3$ mL/well, incubating in carbon dioxide gas incubator at 5% $CO_2$ for 4 days, and then, calculating the number of living cells by the trypan blue staining method using a cytometric plate.

Figure 9:
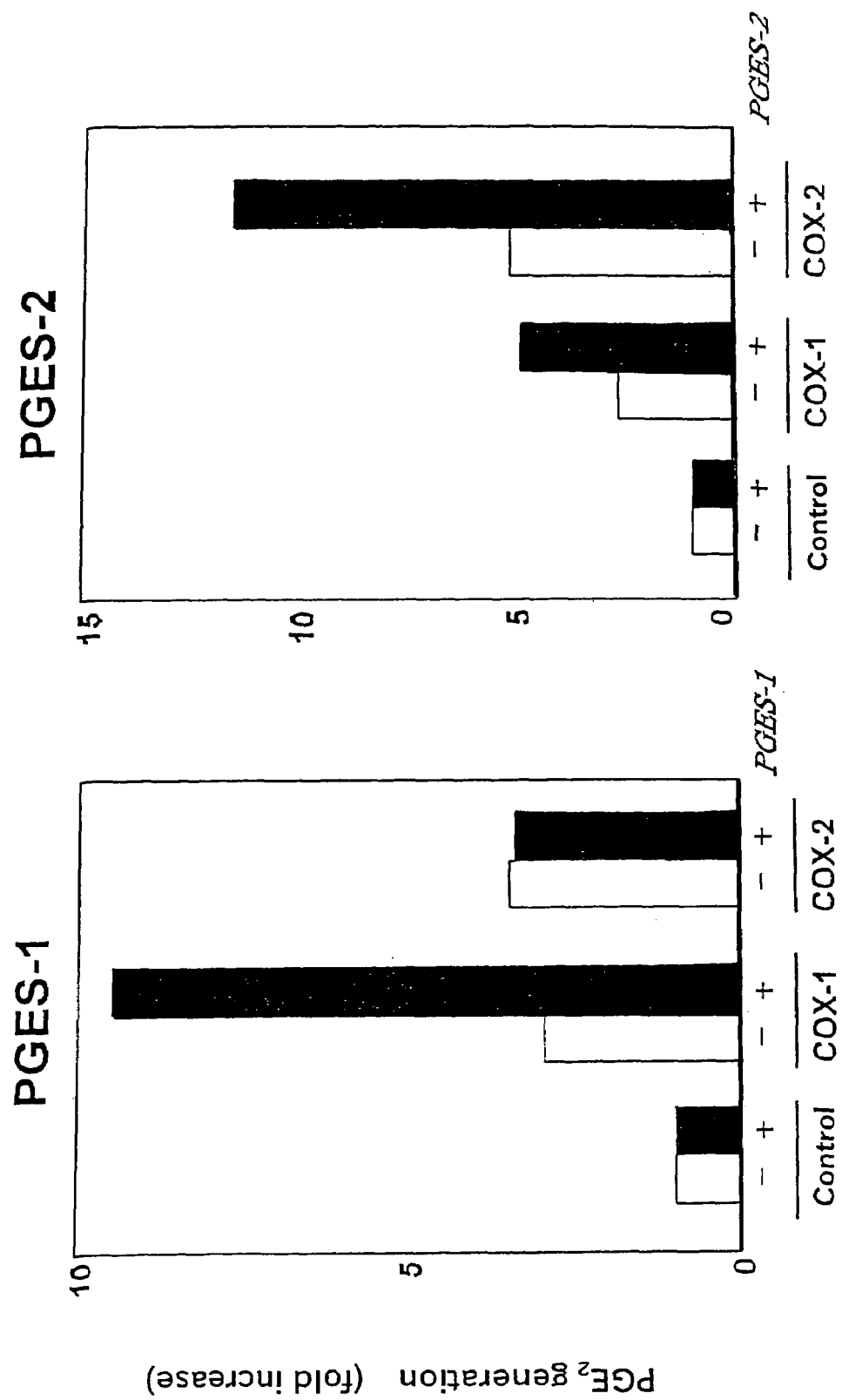
FIG. 9 depicts graphs demonstrating the conversion of added arachidonic acid into $PGE_2$ by PGES-1 or PGES-2. PGES-1 is demonstrated to function by selective coupling with COX-1, and PGES-2 is demonstrated to exhibit an enhanced function by the coupling with COX-2 than with COX-1.
Figure 10:
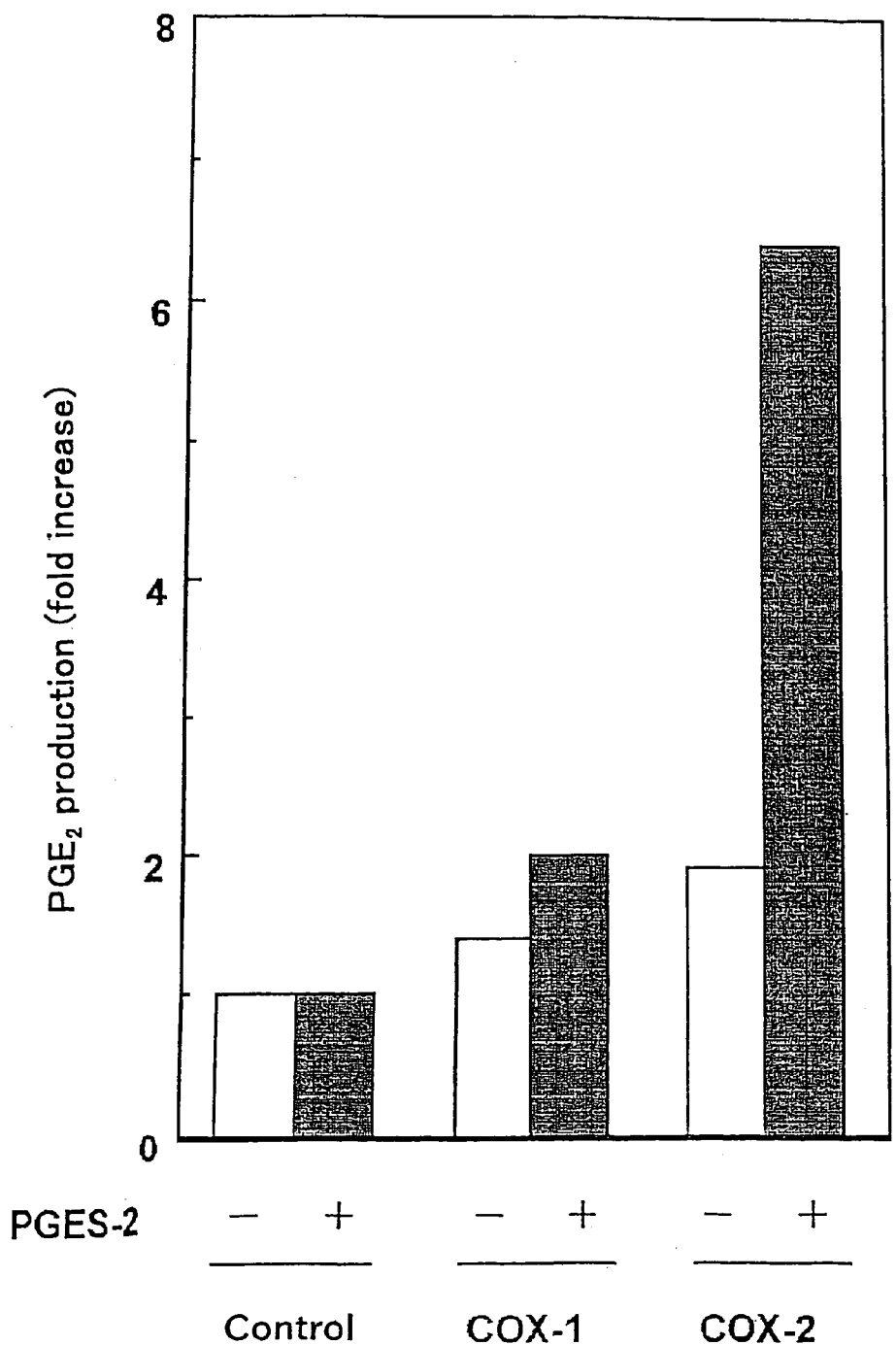
FIG. 10 depicts a graph demonstrating the conversion of endogenous arachidonic acid into $PGE_2$ by PGES-2 in HEK293 transfect cells stimulated with IL-1β.

The PGE2 production level of these cells under a condition adding 2 μmol/L of arachidonic acid to the culture medium was examined. The PGE2 production level of cells coexpressing COX-1 and PGES-1 largely increased compared to cells expressing COX-1 alone, whereas no increase in PGE2 production was observed in cells coexpressing human COX-2 and PGES-1 (FIG. 9, left panel). This suggests the coupling (cooperative functioning) of PGES-1 and COX-1. On the other hand, large amounts of PGE2 was produced by the expression of PGES-2 together with COX-2 (FIG. 9, right panel), suggesting the coupling (cooperative functioning) of PGES-2 and COX-2. A more remarkable increase in PGE2 production by coupling of PGES-2 and COX-2 was demonstrated by stimulating cells with 1 ng/mL human Interleukin-1β (IL-1β; Genzyme) under conditions without the addition of arachidonic acid to the culture medium (FIG. 10).

Figure 11:
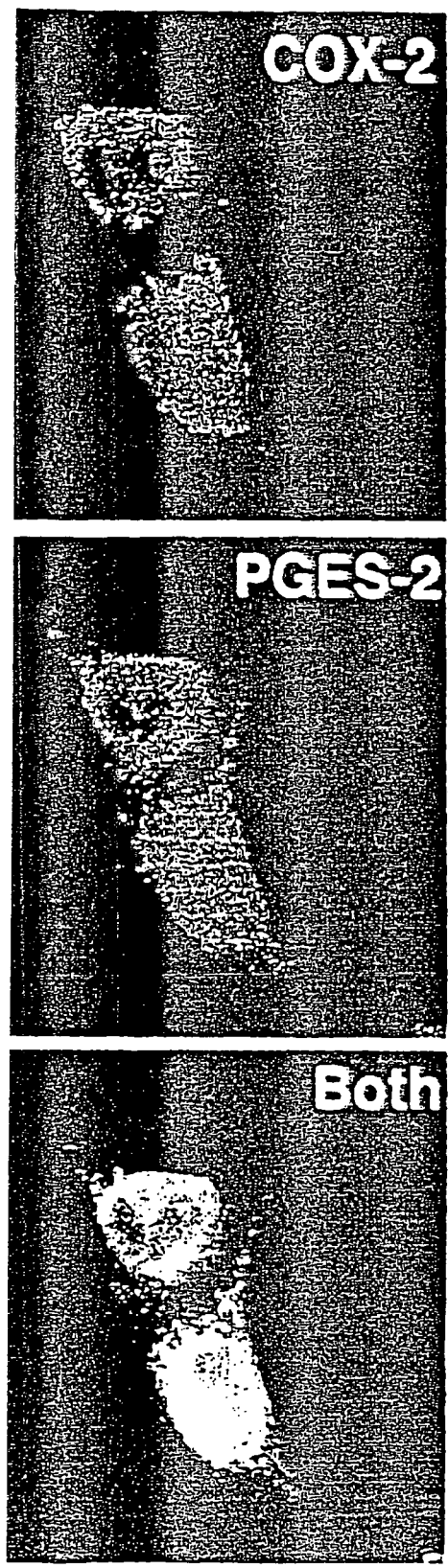
FIG. 11 depicts photographs demonstrating the intracellular distribution of COX-2 and PGES-2. The top panel shows COX-2 distribution, the center panel shows PGES-2 distribution, and the lower panel is an overlay of both of these distributions.

Furthermore, a close relation between COX-2 and PGES-2 was also demonstrated by a similar distribution of the enzymes detected by an indirect immunostaining using a combination of mouse monoclonal antibody against FLAG with FITC-labeled anti-mouse IgG antibody, or goat antisera against COX-2 (Santa Cruz, N-20 goat polyclonal Ab) with Cy3-labeled anti-goat IgG antibody on cells, which cells were prepared to coexpress COX-2 and a fusion protein, consisting of PGES-2 and FLAG, by similarly transfecting an expression vector containing PGES-2 cDNA and FLAG cDNA to cells that express COX-2 alone (FIG. 11).

Figure 12:
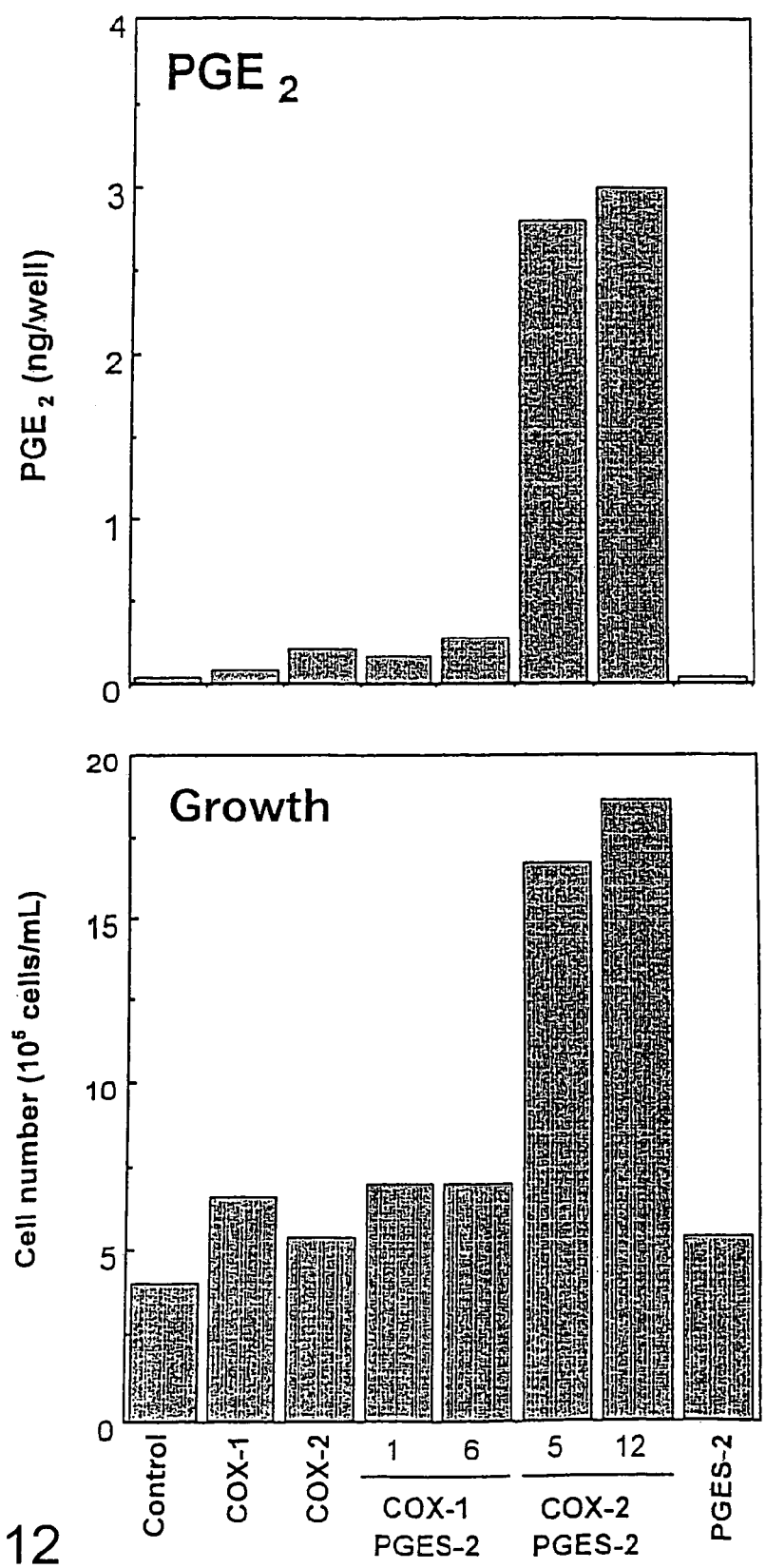
FIG. 12 depicts graphs demonstrating the effect of the coexpression of COX-2 and PGES-2 to enhance $PGE_2$ production and cell proliferation.

Not only PGES but also COX is greatly involved in the pathway to produce PGE2 via the arachidonic acid metabolic pathway. Therefore, when screening for PGES inhibitors using cells, it is preferable to use cells expressing not only PGES but those simultaneously expressing COX. In addition, a phenomenon where both enzymes function cooperatively (coupling) was demonstrated in cells expressing both of COX-1 and PGES-1, and in cells expressing both of COX-2 and PGES-2. Accordingly, actually in vivo, during PGE2 production induced by the stimulus accompanying inflammation, both of COX-2 and PGES-2, or both of COX-1 and PGES-1, are indicated to have an important role functioning cooperatively. Thus, cells expressing these combinations seem to reproduce the situation caused by an inflammatory stimulus in a stabilized form. Furthermore, cell proliferation in addition to PGE2 production is increased by the coexpression of PGES-2 and COX-2 (FIG. 12), which may reflect an aspect of a process where normal cells transform into cancer cells.

INDUSTRIAL APPLICABILITY

The present invention provides a PGES-1 protein having PGE2 synthase activity and genes encoding the protein, which enables the efficient production of PGE2 as well as the efficient screening of PGE2 synthase inhibitors that are useful as anti-inflammatory drugs, and such. Specifically, efficient and accurate screening of PGE2 synthase inhibitors is enabled by cells simultaneously expressing the PGE2 synthase and COX.

The invention claimed is:

1. A method for producing human Prostaglandin E2 (PGE2), the method comprising:
providing a polypeptide comprising the amino acid sequence of SEQ ID NO:1; and
reacting the polypeptide with human Prostaglandin H2 (PGH2).

2. A kit for producing human PGE2, the kit comprising human PGH2 and a polypeptide comprising the amino acid sequence of SEQ ID NO:1.

* * * * *